(12) United States Patent
Takimoto et al.

(10) Patent No.: US 8,093,913 B2
(45) Date of Patent: Jan. 10, 2012

(54) FILM THICKNESS MEASUREMENT DEVICE AND METHOD

(75) Inventors: Hidetoshi Takimoto, Tokorozawa (JP); Takehito Yagi, Odawara (JP); Yoshiyuki Saito, Tokyo (JP); Tsuyoshi Terauchi, Yokohama (JP)

(73) Assignee: IHI Corporation (JP)

( * ) Notice: Subject to any disclaimer, the term of this patent is extended or adjusted under 35 U.S.C. 154(b) by 660 days.

(21) Appl. No.: 12/108,701

(22) Filed: Apr. 24, 2008

(65) Prior Publication Data

US 2009/0267620 A1    Oct. 29, 2009

(51) Int. Cl.
*G01R 27/26* (2006.01)
(52) U.S. Cl. ................ 324/671; 324/686; 324/690
(58) Field of Classification Search .......... 324/671
See application file for complete search history.

(56) References Cited

U.S. PATENT DOCUMENTS

| | | | |
|---|---|---|---|
| 4,482,859 A | | 11/1984 | Fournier ................ 324/61 |
| 5,432,013 A | * | 7/1995 | Tanaka et al. .......... 428/643 |
| 5,531,434 A | * | 7/1996 | Kerschner ............. 271/263 |
| 5,542,289 A | * | 8/1996 | Hool et al. ............. 73/64.52 |
| 5,742,167 A | * | 4/1998 | Haynes ................. 324/671 |
| 5,818,242 A | * | 10/1998 | Grzybowski et al. .... 324/642 |
| 6,442,492 B1 | * | 8/2002 | Jackson et al. ......... 702/31 |
| 2002/0021134 A1 | * | 2/2002 | Stein .................... 324/671 |
| 2003/0056751 A1 | * | 3/2003 | Sukegawa et al. ...... 123/305 |
| 2005/0134293 A1 | * | 6/2005 | Sergoyan et al. ...... 324/662 |

FOREIGN PATENT DOCUMENTS

| | | |
|---|---|---|
| FR | 2506023 | 11/1982 |
| JP | 54-115158 | 9/1979 |
| JP | UM-A-55-139409 | 10/1980 |
| JP | 57-194309 | 11/1982 |
| JP | 59-051301 | 3/1984 |
| JP | UM-A-59-097411 | 7/1984 |
| JP | UM-A-60-036508 | 3/1985 |
| JP | 62-240409 | 10/1987 |
| JP | 01-277604 | 11/1989 |
| JP | 03-225203 | 10/1991 |
| JP | 06-034307 | 2/1994 |
| JP | 08-221683 | 8/1996 |
| JP | 09-189630 | 7/1997 |
| JP | 2001-091205 | 4/2001 |
| JP | 2002-005610 | 1/2002 |
| JP | 2002-140771 | 5/2002 |
| JP | 2003-139732 | 5/2003 |
| JP | 2003-214810 | 7/2003 |
| JP | 2004-169600 | 6/2004 |
| JP | 2005-054773 | 3/2005 |
| JP | 2005-156492 | 6/2005 |
| JP | 2007-506958 | 3/2007 |
| JP | 2007107947 A * | 4/2007 |
| WO | WO 2005/031250 | 4/2005 |

OTHER PUBLICATIONS

Office Action dated Jan. 19, 2010 cited in Canadian counterpart Patent Application No. 2,630,129 (2 pages).
Official Action dated Aug. 31, 2010, cited in counterpart Japanese Patent Application No. 2005-297339.

* cited by examiner

*Primary Examiner* — Timothy J Dole
(74) *Attorney, Agent, or Firm* — Ostrolenk Faber LLP (57) ABSTRACT

A film thickness measurement device, which measures the film thickness of an oil film of lubricating oil, formed in a gap between a piston ring and an electrode provided flush with a piston ring sliding surface of a cylinder liner, by detecting the electrostatic capacitance across the gap, employs an electrostatic capacitance detection portion, which charges the electrostatic capacitance by supplying a constant current to the electrode, detects the electrostatic capacitance based on changes in the charging voltage accompanying the charging, and outputs a detection signal indicating the electrostatic capacitance, and a film thickness computation portion, which calculates the film thickness of the oil film based on the electrostatic capacitance indicated by the detection signal input from the electrostatic capacitance detection portion.

8 Claims, 6 Drawing Sheets

MEASUREMENT POINT X1

FIG. 5B

MEASUREMENT POINT X2

FIG. 5C

MEASUREMENT POINT X3

FIG. 5D

MEASUREMENT POINT X4

FILM THICKNESS MEASUREMENT DEVICE AND METHOD

BACKGROUND OF THE INVENTION

1. Field of the Invention

This invention relates to a film thickness measurement device and method.

The entire contents of Japanese Patent Application No. 2005-297339, filed on Oct. 12, 2005, are incorporated herein by reference.

2. Description of the Related Art

One method of measuring the thickness of an oil film within an engine cylinder during operation entails using a bridge circuit to measure the electrostatic capacitance across the gap between the piston ring and cylinder (more specifically, a sensor electrode provided on the piston ring sliding surface of the cylinder liner), in which the oil film is formed, and calculating the film thickness based on this electrostatic capacitance (see for example Japanese Unexamined Patent Application No. 2003-214810).

In the electrostatic capacitance measurement method using this bridge circuit, a bridge circuit is configured with the gap between the piston ring and the sensor electrode as one capacitor (the measurement capacitance), and with three other reference capacitors; by adjusting the reference capacitors such that the bridge balance condition is satisfied according to the electrostatic capacitance changes of the measurement capacitance, the electrostatic capacitance of the measurement capacitor is determined.

Moreover, a resonant bridge circuit method is another electrostatic capacitance measurement method using a bridge circuit. In this resonant bridge circuit method, the measurement capacitor is positioned in one of the arms of a bridge circuit using resistors, and by varying the power supply frequency while detecting the diagonal potential difference of the bridge circuit, the frequency at which the diagonal potential difference is maximum, that is, the resonance frequency, is determined, and based on this resonance frequency the electrostatic capacitance of the measurement capacitor is computed.

However, when a bridge circuit is used as in the above methods of the prior art, changes in the electrostatic capacitance of the measurement capacitor are very small, so that it has been necessary to position the bridge circuit in the vicinity of the measurement point, that is, the cylinder, due to noise considerations. In this case, the measurement capacitor is exposed to high temperatures, so that the electrostatic capacitance of the measurement capacitor changes due to temperature dependence, and error occurs in the measured results for the electrostatic capacitance of the measurement capacitor; consequently there is the problem that measurement errors occur in the measured thickness of the oil film.

Moreover, when the resonant bridge circuit method is used, by using resistors with a comparatively low temperature dependence as circuit elements, measurement errors due to temperature can be alleviated; but because the power supply frequency must be varied to determine the resonance frequency, high-speed measurement (realtime measurement) is difficult, and so there are the problems that the measurement device configuration is complex and costly, and in addition that time is required to perform judgments.

SUMMARY OF THE INVENTION

This invention has as an object the realtime measurement, with good accuracy and at low cost, of the film thickness of an oil film on a piston ring sliding surface within an engine cylinder.

This invention relates to a film thickness measurement device, which measures the film thickness of an oil film of lubricating oil formed in a gap between a piston ring and an electrode provided flush with a piston ring sliding surface of a cylinder liner, by detecting the electrostatic capacitance across the gap, and employs an electrostatic capacitance detection portion, which charges the electrostatic capacitance by supplying a constant current to the electrode, detects the electrostatic capacitance based on changes in the charging voltage accompanying the charging, and outputs a detection signal indicating the electrostatic capacitance, and a film thickness computation portion, which calculates the film thickness of the oil film based on the electrostatic capacitance indicated by the detection signal input from the electrostatic capacitance detection portion.

Further, in a film thickness measurement device of this invention, it is desirable that the film thickness computation portion calculate the difference between the electrostatic capacitance detected in the state in which the electrode is opposed to the piston ring and the electrostatic capacitance in a state in which the electrode and the piston ring are not opposed.

Further, in a film thickness measurement device of this invention, it is desirable that the electrode be press-fitted into a penetrating hole which penetrates from the outer-wall side of the cylinder liner toward the piston ring sliding surface so as to be flush with the piston ring sliding surface, that the electrode be covered with an insulating inner layer, that the inner layer be further covered with a conductive outer layer, and that the outer layer be grounded in common with the ground portion of the electrostatic capacitance detection portion.

Further, in a film thickness measurement device of this invention, it is desirable that a crank rotation angle detection portion, which detects a crank rotation angle indicating the position of the piston ring relative to the piston ring sliding surface, be employed, and that the film thickness computation portion calculate the film thickness of the oil film in synchronization with the crank rotation angle detected by the crank rotation angle detection portion.

Further, in a film thickness measurement device of this invention, it is desirable that the electrostatic capacitance detection portion output the detection signal to the film thickness computation portion as a current signal.

Further, this invention relates to a film thickness measurement method, in which the film thickness of an oil film of lubricating oil formed in a gap between a piston ring and an electrode provided flush with a piston ring sliding surface of a cylinder liner is detected by measuring the electrostatic capacitance across the gap, and has a first process of charging the electrostatic capacitance by supplying a constant current to the electrode; a second process of detecting the electrostatic capacitance based on changes in the charging voltage accompanying charging; and a third process of calculating the film thickness of the oil film based on the electrostatic capacitance.

Further, in a film thickness measurement method of this invention, it is desirable that in the third process, the film thickness of the oil film be calculated based on the difference between the electrostatic capacitance detected in the state in which the electrode and the piston ring are opposed and the electrostatic capacitance in a state in which the electrode and the piston ring are not opposed.

Further, in a film thickness measurement method of this invention, it is desirable that the electrode be press-fitted into a penetrating hole which penetrates from the outer-wall side of the cylinder liner toward the piston ring sliding surface so as to be flush with the piston ring sliding surface, that the electrode be covered with an insulating inner layer, that the inner layer be further covered with a conductive outer layer, and that the outer layer be grounded in common with the detection circuit which performs the first process and the second process.

Further, in a film thickness measurement method of this invention, it is desirable that in the third process, the film thickness of the oil film be calculated in synchronization with a crank rotation angle indicating the position of the piston ring.

Further, in a film thickness measurement method of this invention, it is desirable that the detection signal indicating the electrostatic capacitance and obtained in the second process be output to the third process as a current signal.

In this invention, in order to detect the electrostatic capacitance across the gap between the piston ring and the electrode provided flush with the piston ring sliding surface of the cylinder liner, means are adopted such that the electrostatic capacitance is charged by supplying a constant current to the electrode, and the electrostatic capacitance is detected based on changes in the charging voltage accompanying the charging. Hence there is no need for reference capacitors such as in bridge circuits of the prior art. Therefore, the effect of the ambient temperature is reduced, so that the electrostatic capacitance, that is, the film thickness of the oil film, can be measured with good accuracy.

Moreover, because a measurement device with a complex configuration such as when using a resonant bridge circuit method of the prior art is not necessary, costs can be reduced.

DESCRIPTION OF THE PREFERRED EMBODIMENTS

Below, an embodiment of the invention is explained referring to the drawings.

Figure 1:
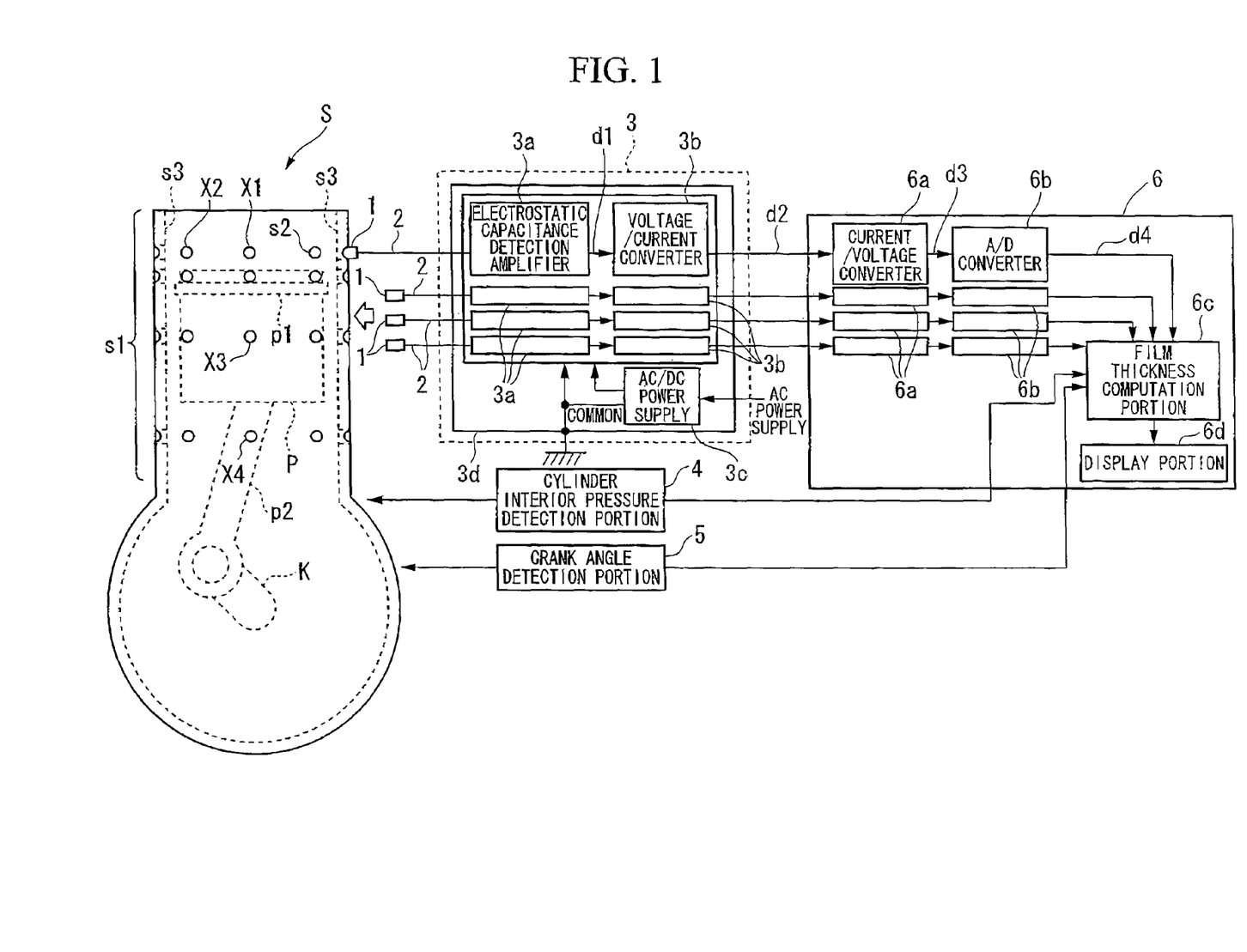
FIG. 1 shows the device configuration of the film thickness measurement device in accordance with an embodiment of the invention.

FIG. 1 shows the device configuration of the film thickness measurement device of an embodiment of the invention As shown in the figure, the film thickness measurement device employs a sensor head 1, coaxial cable 2, electrostatic capacitance detection portion 3, cylinder interior pressure detection portion 4, crank angle detection portion 5, and signal processing portion 6. Such a film thickness measurement device measures the thickness of the oil film of lubricating oil formed in the gap between the inner wall of a cylinder liner s1 (piston sliding surface s3) and a piston ring p1 in the engine cylinder S.

This engine cylinder S is for example a cylinder in a four-cycle engine, and as shown, has a cylinder liner s1, sensor head mounting hole s2, piston sliding surface s3, piston P, piston ring p1, piston rod p2, and crankshaft K. These constituent elements are, except for the sensor head mounting hole s2, all well-known, and so detailed explanations are omitted. In general, the outer-wall side of an engine cylinder S is water-cooled, but the temperature on the inner wall side reaches 200° C. or higher. That is, the ambient temperature of an engine cylinder S is high.

The sensor head mounting hole s2 is a hole used to mount the sensor head 1 of the film thickness measurement device, and penetrates from the outer-wall side of the cylinder liner s1 toward the piston sliding surface s3. A plurality of sensor head mounting holes S2 are provided at prescribed intervals in the outer circumferential direction of the cylinder liner s1, and in a plurality of stages at a prescribed interval in the piston sliding direction of the cylinder liner s1.

Figure 2:
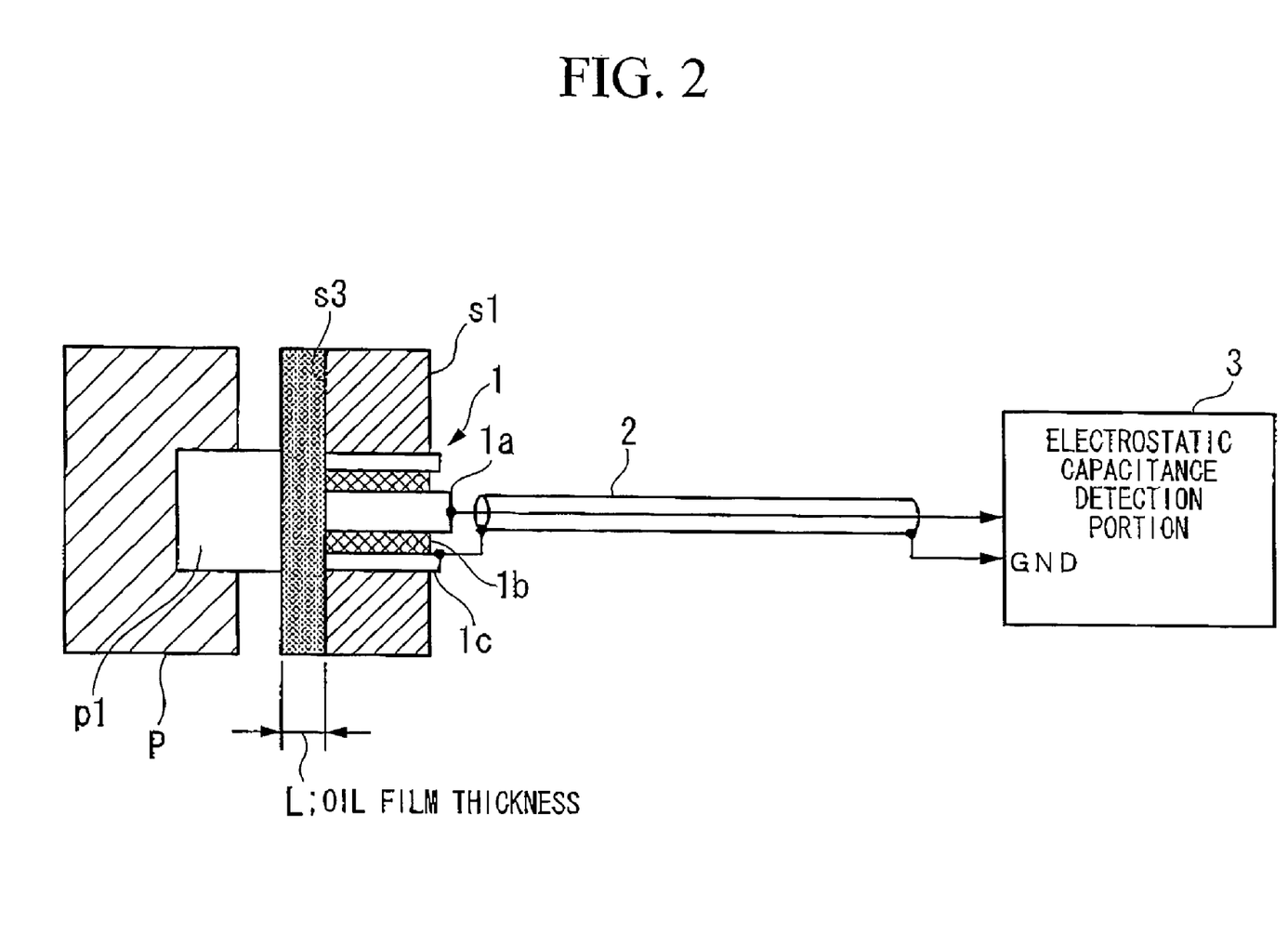
FIG. 2 is an enlarged view of the mounting position of a sensor head 1 in accordance with an embodiment of the invention.

As shown in FIG. 2, the sensor head 1 has a construction in which a cylindrical sensor electrode 1a is covered by an insulating member 1b in a concentric shape, and the outer periphery of the insulating member 1b is further covered by a conducting sensor case 1c in a concentric shape. This sensor head 1 is press-fitted into the sensor mounting hole s2 so as to be flush with the piston sliding surface s3. When the sensor electrode 1a is opposed to the piston ring p1, the sensor electrode 1a, piston ring p1, and the oil film forms a capacitor (measurement capacitor). The piston ring p1 serves as the opposing electrode, and the oil film serves as a dielectric member.

This sensor electrode 1a is connected to the electrostatic capacitance detection portion 3 (specifically, the electrostatic capacitance detection amplifier 3a) via the coaxial cable 2. As shown in FIG. 2, one end of the braided wire forming the shield layer of the coaxial cable 2 is connected to the sensor case 1c of the sensor head 1, and the other end is connected to the ground portion (GND, ground) of the electrostatic capacitance detection portion 3. By this means, the sensor case 1c and electrostatic capacitance detection portion 3 have a common ground.

The electrostatic capacitance detection portion 3 has an electrostatic capacitance detection amplifier 3a, voltage/current converter 3b, AC/DC power supply 3c, and shield case 3d.

The electrostatic capacitance detection amplifier 3a supplies a constant current to the sensor electrode 1a of the sensor head 1 via the coaxial cable 2, and based on changes in the charging voltage of the measurement capacitor being charged by this constant current, detects the electrostatic capacitance Cx of the measurement capacitor, and outputs a voltage signal d1 (an analog signal) indicating the electrostatic capacitance Cx to the voltage/current converter 3b. The voltage/current converter 3b converts the voltage signal d1 input from the electrostatic capacitance detection amplifier 3a into a current signal d2, and outputs the result to the signal processing portion 6 (specifically, the current/voltage converter 6a).

The AC/DC power supply 3c converts AC power supplied from outside into DC power, which is supplied to the electrostatic capacitance detection amplifier 3a and voltage/current converter 3b. The common terminal of this AC/DC power supply 3c is connected to the shield case 3d. The shield case 3d is an electromagnetic shielding housing which accommodates the electrostatic capacitance detection amplifier 3a, voltage/current converter 3b, and AC/DC power supply 3c, and is externally grounded.

The electrostatic capacitance detection portion 3 has a prescribed number of the above-described electrostatic capacitance detection amplifiers 3a and voltage/current converters 3b, which detect the electrostatic capacitance Cx at the mounting positions of each sensor head 1, and output voltage signals d1 indicating the electrostatic capacitance Cx to the respective voltage/current converters 3b. Although not shown in the figure, this film thickness measurement device has a plurality of electrostatic capacitance detection portions 3 according to the number of sensor heads 1.

The cylinder internal pressure detection portion 4 detects the pressure within the combustion chamber of the engine cylinder S, and outputs to the signal processing portion 6 (specifically, to the film thickness computation portion Gc) a pressure signal indicating the pressure. The crank angle detection portion 5 is for example an encoder, which detects the rotation angle of the crankshaft K, and outputs a rotation angle signal indicating this rotation angle to the signal processing portion 6 (specifically, to the film thickness computation portion 6c). This rotation angle of the crankshaft indicates the position of the piston ring p1 in the piston sliding direction.

The signal processing portion 6 has a current/voltage converter 6a, A/D converter 6b, film thickness computation portion 6c, and display portion 6d.

In the signal processing portion 6, the current/voltage converter 6a converts the current signal d2 input from the voltage/current converter 3b of the electrostatic capacitance detection portion 3 into a voltage signal d3, which is output to the A/D converter 6b. The A/D converter 6b converts the voltage signal d3, which is an analog signal, into a digital signal d4, and outputs the result to the film thickness computation portion 6c.

The film thickness computation portion 6c calculates the film thickness of the oil film formed in the gap between the piston ring p1 and the sensor electrode 1a, by performing prescribed signal processing of the digital signal d4 input from the A/D converter 6b (that is, the electrostatic capacitance Cx), the pressure signal input from the cylinder internal pressure detection portion 4, and the rotation angle signal input form the crank angle detection portion 5, and outputs a film thickness signal indicating the film thickness to the display portion 6d. The display portion 6d is for example a liquid crystal display device, and displays the film thickness information based on the above film thickness signal.

Next, film thickness measurement operation of a film thickness measurement device configured as described above is explained.

As is well known, an engine cylinder S repeats a combustion stroke, exhaust stroke, intake stroke, and compression stroke with a prescribed period, and the piston P undergoes reciprocating motion within the cylinder liner s1, And as shown in FIG. 2, when the piston ring p1 and the sensor electrode 1a of the sensor head 1 are opposed, a measurement capacitor is formed with the oil film formed in the gap between the sensor electrode 1a and the piston ring p1 as a dielectric member. Hence by detecting the electrostatic capacitance Cx between this sensor electrode 1a and piston ring p1, the film thickness L of the oil film can be determined.

Figure 3A:
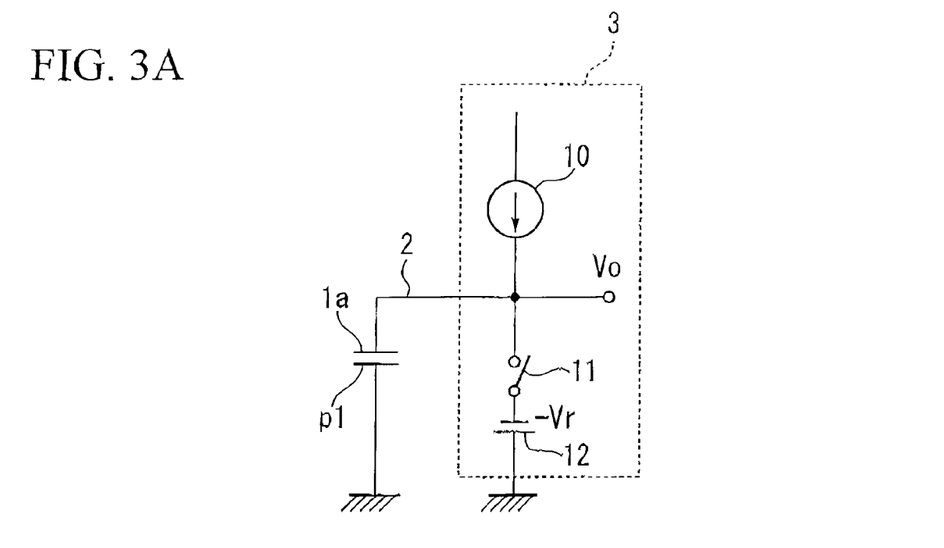
FIG. 3A and FIG. 3B explain the principle of electrostatic capacitance detection in accordance with an embodiment of the invention.
Figure 3B:
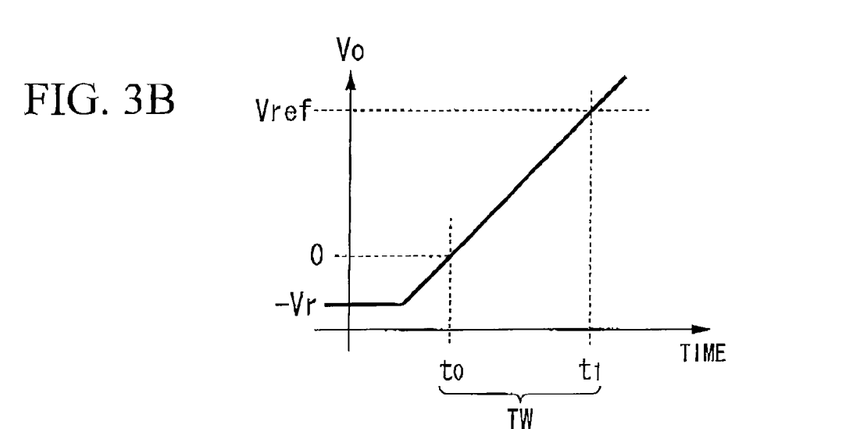

The principle of electrostatic capacitance detection in the electrostatic capacitance detection amplifier 3a is explained using FIG. 3A and FIG. 3B. FIG. 3A shows in summary equivalent circuits of the electrostatic capacitance detection amplifier 3a and measurement capacitor. As shown in the figure, by supplying constant current from a constant current supply 10 to the sensor electrode 1a via the coaxial cable 2, the measurement capacitor is charged. FIG. 3B shows the change with time in the charging voltage V0 at this time. The electrostatic capacitance Cx of the measurement capacitor can be calculated from the charging time Tw for the charging voltage V0 to rise from 0 V to a prescribed voltage value (Vref) Here, for measuring the electrostatic capacitance Cx in succession, the charged electric charge needs to be discharged. Hence by turning on a reset switch 11 with a prescribed period and applying a negative voltage (−Vr) to the measurement capacitor from a reset power supply 12, electric charge is discharged.

In general, the electrostatic capacitance Cx is approximately 50 to 100 pF, so that in measuring the electrostatic capacitance Cx as described above, it is desirable that the coaxial cable 2 be made as short as possible in order to improve measurement accuracy, and to this end the electrostatic capacitance detection portion 3 is positioned close to the engine cylinder S. When the electrostatic capacitance detection portion 3 is positioned in a location at a high ambient temperature, if a bridge circuit is used to detect the electrostatic capacitance Cx as in the prior art, accurate detection is not possible due to the temperature dependence of the reference capacitors. However, in this embodiment, a detection method which does not employ a bridge circuit is adopted, so that detection can be performed with good accuracy, regardless of the ambient temperature.

Further, the sensor case 1c which is the external conductor of the sensor head 1 and the electrostatic capacitance detection portion 3 are grounded in common, so that the effect of noise can be reduced, and moreover interference due to leakage electric fields between sensor heads 1 in proximity can be suppressed, so that the detection accuracy can be improved when the electrostatic capacitance Cx is detected at a plurality of positions in particular, as in this embodiment.

Figure 4:
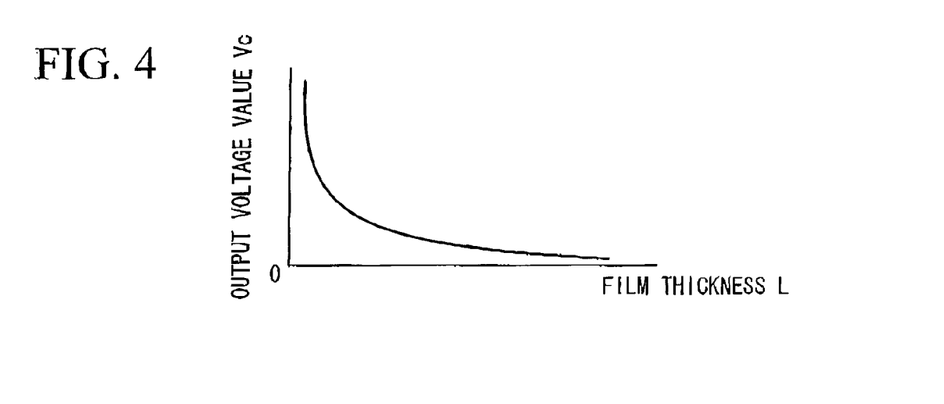
FIG. 4 is an output voltage characteristic diagram for the electrostatic capacitance detection amplifier 3a in accordance with an embodiment of the invention.

The electrostatic capacitance detection amplifier 3a detects the electrostatic capacitance Cx of a measurement capacitor based on the principle of electrostatic capacitance detection described above, and outputs a voltage signal d1 indicating the electrostatic capacitance Cx to the voltage/current converter 3b. FIG. 4 shows the output voltage characteristic of an electrostatic capacitance detection amplifier 3a.

In this figure, the horizontal axis indicates the film thickness L of the oil film, and the vertical axis gives the voltage value of the voltage signal d1 (the output voltage value Vc). As indicated in the figure, the output voltage value Vc of the electrostatic capacitance detection amplifier 3a is larger when the film thickness L is smaller (that is, when the electrostatic capacitance Cx is higher), and is smaller when the film thickness L is larger (that is, when the electrostatic capacitance Cx is lower).

Figure 5A:
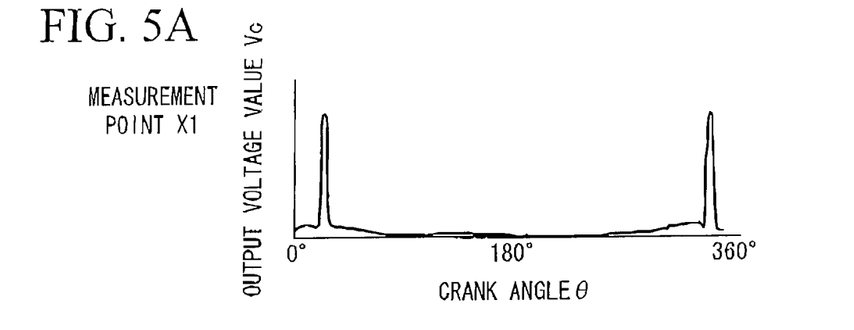
FIG. 5A through FIG. 5D are diagrams indicating the relation between the output voltage value Vc and crankshaft rotation angle (crank angle θ) in accordance with an embodiment of the invention.
Figure 5B:
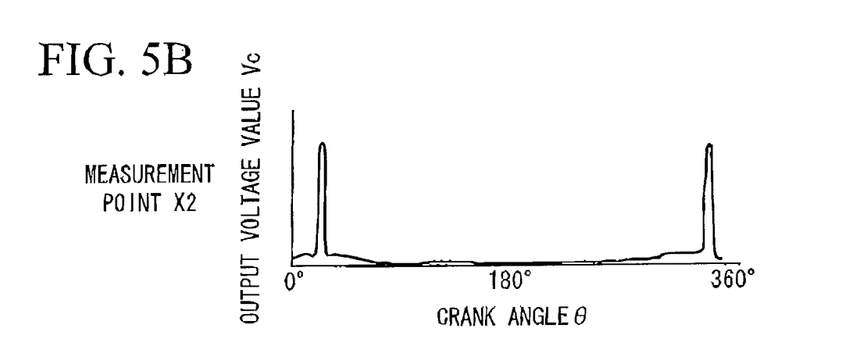
Figure 5C:
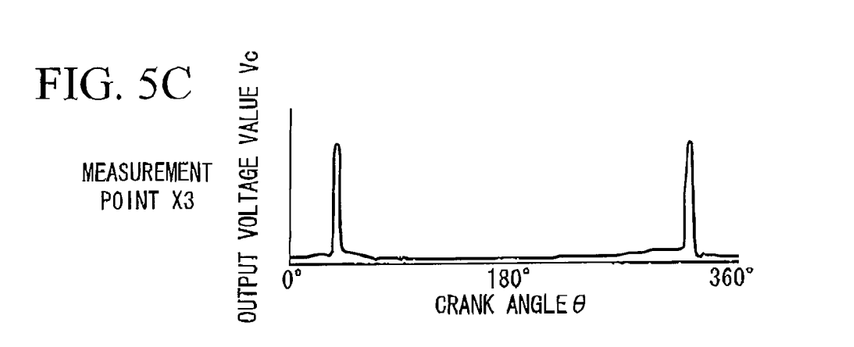
Figure 5D:
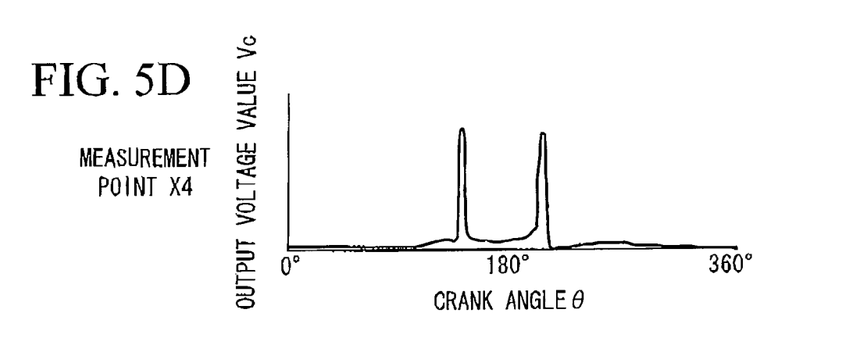

The relation between the output voltage value Vc described above and the crankshaft rotation angle (crank angle θ) appears in FIG. 5A through FIG. 5D. FIG. 5A shows the output voltage value Vc, indicating the electrostatic capacitance Cx detected at measurement point X1 in FIG. 1, and FIG. 5B, FIG. 5C, and FIG. 5D show the output voltage values Vc indicating the electrostatic capacitances Cx detected at measurement points X2, X3, and X4, respectively, In FIG. 5A through FIG. 5D, when the crankshaft rotation angle is 0°, the piston P is positioned at top dead center, and when the crankshaft rotation angle is 180°, the piston P is positioned at bottom dead center.

As shown in FIG. 5A through FIG. 5D, at each of the measurement points, the output voltage value Vc is highest at a prescribed crank angle θ. The output voltage value Vc is highest in this way when the electrostatic capacitance Cx is highest, that is, when the sensor head 1 provided at the measurement point is opposed to the piston ring p1. This relation between the output voltage value Vc and crank angle θ is determined uniquely for each position of the measurement points. Hence by determining in advance for each measurement point the crank angle (opposing rotation angle θc) when the sensor head 1 and the piston ring p1 are opposed, monitoring the crank angle θ and extracting the output voltage value Vc when the crank angle θ is equal to the opposing rotation angle θc, and converting the output voltage value Vc into an electrostatic capacitance Cx, the thickness L of the oil film formed in the gap between the sensor head 1 and the piston ring can be calculated from this electrostatic capacitance Cx.

The voltage/current converter 3b converts the voltage signal d1 input from the electrostatic capacitance detection amplifier 3a into a current signal d2, which is output to the current/voltage converter 6a of the signal processing portion 6. The signal processing portion 6 is placed at a position distant from the engine cylinder S, and so the wire connecting the electrostatic capacitance detection portion 3 and the signal processing portion 6 is long. When transmitting information by means of voltage signals over such a long wire, the voltage signals are easily affected by noise, so that accurate information transmission is difficult. Hence in this embodiment, as explained above, the voltage signals d1 are first converted into current signals d2 and transmitted, to reduce the effect of noise.

The current/voltage converter 6a converts the current signal d2 back into a voltage signal d3, which is output to the A/D converter 6b. Here, the voltage value of a voltage signal d3 is the same value as the output voltage value Vc of the voltage signal d1. The A/D converter 6b converts the voltage signal d3, which is an analog signal, into a digital signal d4, and outputs the result to the film thickness computation portion 6c.

Figure 6:
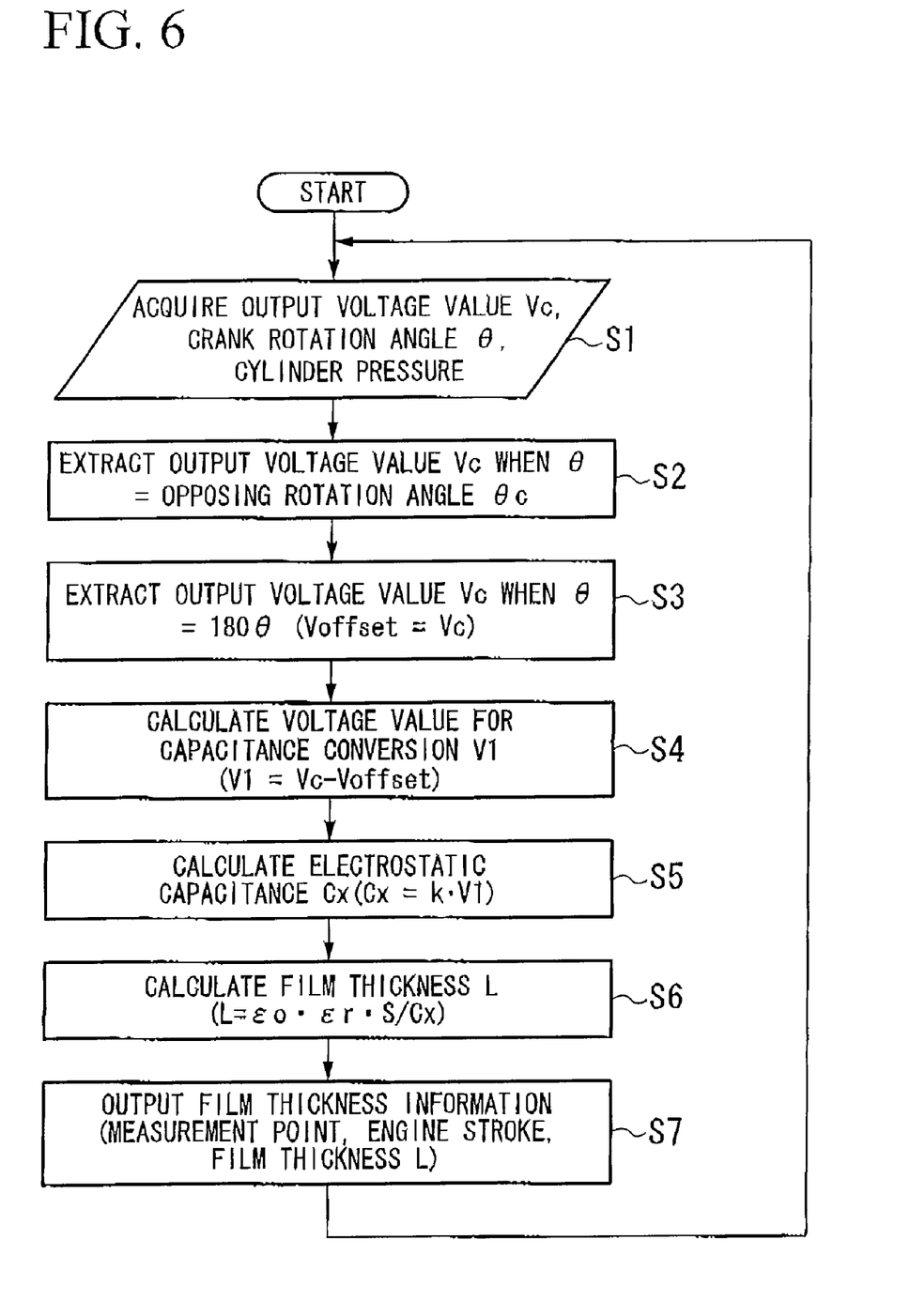
FIG. 6 is a flowchart of operation of the film thickness computation portion 6c in accordance with an embodiment of the invention; and, FIG. 7 shows the relation between output voltage value Vc for measurement point X1 and crank angle θ as well as strokes, in accordance with an embodiment of the invention.

Next, the operation flowchart of FIG. 6 is used to explain film thickness computation processing in the film thickness computation portion 6c. In order to simplify the following explanation, film thickness computation processing is explained for a measurement point X1. First, the film thickness computation portion 6c acquires the digital signal (output voltage value Vc) indicating the electrostatic capacitance Cx detected for measurement point X1, as described above, and in addition acquires the pressure within the cylinder (cylinder pressure) from the cylinder interior pressure detection portion 4, and the crank angle θ from the crank angle detection portion 5 (step S1).

Figure 7:
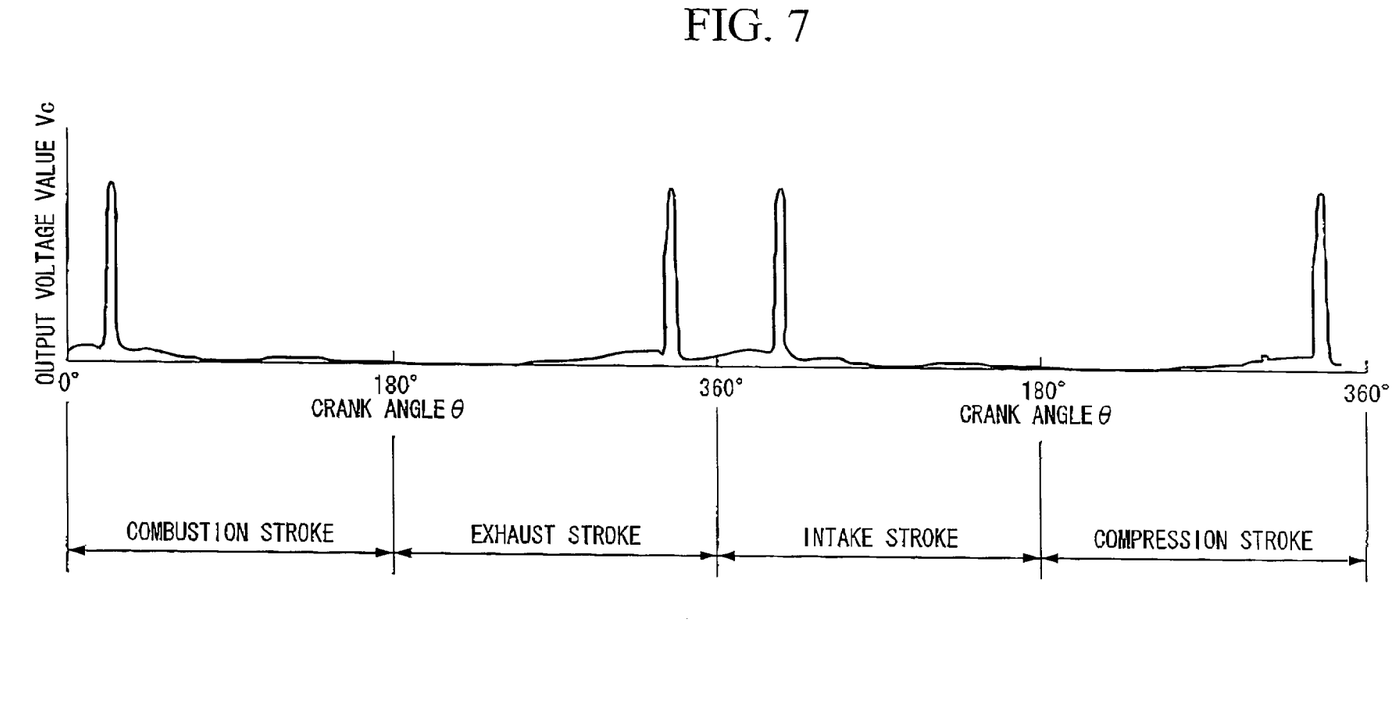

Then, the film thickness computation portion 6c compares the opposing rotation angle θc at measurement point X1, stored in advance, with the crank angle θ, and when the two are equal, extracts the output voltage value Vc. At the same time, the film thickness computation portion 6c judges from the cylinder pressure whether the timing of extraction of the output voltage value Vc is during a combustion stroke, an exhaust stroke, an intake stroke, or a compression stroke (step S2). FIG. 7 shows the relation between the output voltage value Vc extracted in this way, the crank angle θ, and the different strokes. As is shown in the figure, an output voltage value Vc is extracted once in each stroke.

The electrostatic capacitance Cx actually detected by the electrostatic capacitance detection amplifier 3a is expressed as the sum of the electrostatic capacitance due to the oil film and the electrostatic capacitance of the coaxial cable 2. Compared with the electrostatic capacitance due to the oil film (approximately several tens to several hundreds of picofarads), the electrostatic capacitance of the coaxial cable 2 is approximately the same value, and so cannot be ignored. Further, the electrostatic capacitance of the coaxial cable 2 has a temperature dependence, and so the electrostatic capacitance value changes with changes in the ambient temperature. For these reasons, if the output voltage value Vc determined in step S2 is simply converted into an electrostatic capacitance Cx, an extremely large measurement error occurs. Hence the electrostatic capacitance of the coaxial cable 2 must be taken into account, and the output voltage value Vc must be corrected.

Hence the film thickness computation portion 6c extracts the output voltage value Vc when the crank angle θ=180° and uses this as an offset voltage Voffset=Vc (step S3), and calculates the voltage for capacitance conversion V1 (=Vc−Voffset) from the difference between the output voltage value Vc extracted in step S2 and the offset voltage Voffset (step S4).

Thus when the crank angle θ=180°, the piston P exists at bottom dead center, so that the sensor head 1 mounted at measurement point X1 and the piston ring p1 are not opposed. At this time, the electrostatic capacitance due to the oil film can be regarded as substantially zero, so that the electrostatic capacitance Cx measured at measurement point X1 is only the electrostatic capacitance due to the coaxial cable 2. Hence the offset voltage Voffset is an output voltage value indicating the electrostatic capacitance of the coaxial cable 2. Consequently the voltage value for capacitance conversion V1 is the value resulting when the electrostatic capacitance of the coaxial cable 2 is removed from the electrostatic capacitance Cx detected by the electrostatic capacitance detection amplifier 3a. By this means the effect of the electrostatic capacitance of the coaxial cable 2 can be decreased, and so the accuracy of detection of the electrostatic capacitance Cx can be improved.

Next, the film thickness computation portion 6c calculates the electrostatic capacitance Cx (=k·V1) by multiplying the voltage value for capacitance conversion V1 by a capacitance conversion coefficient k (step S5), and calculates the film thickness L of the oil film based on the following formula (equation (1)) between the electrostatic capacitance Cx, the permittivity of vacuum $\epsilon_0$, the relative permittivity of the lubricating oil $\epsilon r$, and the area S of the sensor electrode 1a of the sensor head 1 (the area opposing the piston ring p1) (step S6).

$$L = \epsilon_0 \cdot \epsilon r \cdot S / Cx \qquad (1)$$

Then, the film thickness computation portion 6c takes the position of the measurement point, the stroke, and the film thickness L as one set of film thickness information, and outputs a film thickness signal indicating this film thickness information to the display portion 6d (step S7). The display portion 6d displays the film thickness information based on this film thickness signal. The film thickness computation portion 6c repeats the operations of steps S1 through S7 for measurement points mounted on each sensor head 1, and calculates film thicknesses L for the oil film at each measurement point.

In the above embodiment, the film thickness computation portion 6c extracts the output voltage value Vc when the crank angle θ=180° for use as the offset voltage Voffset=Vc; however, this crank angle θ is not limited to 180°, and any crank angle θ can be used which indicates that the piston ring p1 is at a position at which the electrostatic capacitance due to the oil film can be regarded as substantially zero. Further, a judgment may be made, from the value of the calculated film thickness L, as to whether an oil film is formed, or as to whether the piston ring p1 and cylinder liner s1 are in contact, and an alarm may be output when it is judged that an oil film is not formed, or that the piston ring p1 and cylinder liner s1 are in contact.

As explained above, by means of this embodiment, the effects of the ambient temperature, the electrostatic capacitance of the coaxial cable 2, and mutual interference between the plurality of sensor heads 1 are reduced, so that the electrostatic capacitance Cx can be detected with good accuracy, and as a result the film thickness L of the oil film can be measured with good accuracy.

In the above, a preferred embodiment of the invention has been explained, but the invention is not limited to this embodiment. Various additions, omissions, substitutions, and other modifications can be made, without deviating from the gist of the invention. The invention is not limited by the above explanations, but is limited only by the scope of the attached claims.

What is claimed is:

1. A film thickness measurement device, which measures the film thickness of an oil film of lubricating oil formed in a gap between a piston ring and one or a plurality of electrodes provided flush with a piston ring sliding surface of a cylinder liner, by detecting the electrostatic capacitance across the gap, the device comprising:
   an electrostatic capacitance detection portion, which charges the electrostatic capacitance by supplying a constant current to the electrode, detects the electrostatic capacitance based on changes in the charging voltage accompanying the charging, and outputs a detection signal indicating the electrostatic capacitance;
   a film thickness computation portion, which calculates the film thickness of the oil film based on the electrostatic capacitance indicated by the detection signal input from the electrostatic capacitance detection portion; and
   a crank rotation angle detection portion which detects the crank rotation angle indicating the position of the piston ring with respect to the piston ring sliding surface,
   wherein the film thickness computation portion calculates the film thickness of the oil film in synchronization with the crank rotation angle detected by the crank rotation angle detection portion.

2. The film thickness measurement device according to claim 1, wherein the film thickness computation portion calculates the film thickness of the oil film based on a difference between the electrostatic capacitance detected in a state in which the electrode and piston ring are opposed and the electrostatic capacitance detected in a state in which the electrode and piston ring are not opposed.

3. The film thickness measurement device according to claim 1, further comprising an insulating inner layer positioned to cover the electrode, and a conductive outer layer positioned to cover the insulating inner layer,
   wherein the cylinder liner, includes an outer wall on an opposite side of the cylinder liner than the sliding surface, and the electrostatic capacitance detection portion includes a ground portion, and
   the electrode is press-fitted into a penetrating hole, which penetrates from the outer-wall side of the cylinder liner toward the piston ring sliding surface so as to be flush with the piston ring sliding surface; and
   the outer layer is grounded in common with the ground portion of the electrostatic capacitance detection portion.

4. The film thickness measurement device according to claim 1, wherein the electrostatic capacitance detection portion outputs the detection signal as a current signal to the film thickness computation portion.

5. A film thickness measurement method for detecting a film thickness of an oil film of lubricating oil formed in a gap between a piston ring and an electrode provided flush with a piston ring sliding surface of a cylinder liner, by measuring the electrostatic capacitance across the gap, the method comprising:
   a first process of charging the electrostatic capacitance by supplying a constant current to the electrode;
   a second process of detecting the electrostatic capacitance by measuring the electrostatic capacitance across the gap based on changes in a charging voltage accompanying the charging; and,
   a third process of calculating the film thickness of the oil film based on the measured electrostatic capacitance, where the calculating of the film thickness of the oil film is performed in synchronization with a crank rotation angle indicating the position of the piston ring.

6. The film thickness measurement method according to claim 5, wherein the piston ring and the electrode have a state at which they are opposed and a state at which they are not opposed, and
   in the third process, the film thickness of the oil film is calculated based on a difference between the electrostatic capacitance detected in the state in which the electrode and piston ring are opposed and the electrostatic capacitance in the state in which the electrode and piston ring are not opposed.

7. The film thickness measurement method according to claim 5, wherein:
   the electrode is press-fitted into a penetrating hole which penetrates from the outer-wall side of the cylinder liner toward the piston ring sliding surface so as to be flush with the piston ring sliding surface;
   the electrode is covered with an insulating inner layer and the inner layer is further covered with a conductive outer layer; and
   the outer layer is grounded in common with a detection circuit which performs the first process and the second process.

8. The film thickness measurement method according to claim 5, wherein detection signals indicating electrostatic capacitance are obtained in the second process and are supplied to the third process as current signals representing the measured electrostatic capacitance.

* * * * *